US012694989B2

(12) United States Patent
Wang et al.

(10) Patent No.: US 12,694,989 B2
(45) Date of Patent: Jul. 28, 2026

(54) APPARATUS AND METHOD FOR MODERATING A SKIN LESION DETECTION MODEL

(71) Applicant: KONINKLIJKE PHILIPS N.V., Eindhoven (NL)

(72) Inventors: Lu Wang, Eindhoven (NL); Bastiaan Wilhelmus Maria Moeskops, Uden (NL); Erik Gosuinus Petrus Schuijers, Breda (NL); Jonathan Alambra Palero, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 299 days.

(21) Appl. No.: 18/269,105

(22) PCT Filed: Dec. 7, 2021

(86) PCT No.: PCT/EP2021/084507
§ 371 (c)(1),
(2) Date: Jun. 22, 2023

(87) PCT Pub. No.: WO2022/144150
PCT Pub. Date: Jul. 7, 2022

(65) Prior Publication Data
US 2024/0304337 A1       Sep. 12, 2024

(30) Foreign Application Priority Data

Dec. 29, 2020     (EP) ..................................... 20217603

(51) Int. Cl.
*G16H 50/50*       (2018.01)
*A61B 5/00*        (2006.01)
(Continued)

(52) U.S. Cl.
CPC ............. *G16H 50/50* (2018.01); *A61B 5/444* (2013.01); *A61B 5/742* (2013.01); *A61B 5/746* (2013.01);
(Continued)

(58) Field of Classification Search
None
See application file for complete search history.

(56) References Cited

U.S. PATENT DOCUMENTS 5,913,686 A      6/1999   Van Winkle
10,878,567 B1 *  12/2020  Abid .................... A61B 5/7267
(Continued)

FOREIGN PATENT DOCUMENTS

CN       108629236 A     10/2018
CN       109345480 A     2/2019
(Continued)

OTHER PUBLICATIONS

International Search Report and Written Opinion of PCT/EP2021/084507, dated Feb. 22, 2022.
(Continued)

*Primary Examiner* — Thomas D Lee

(57) ABSTRACT

According to an aspect, there is provided an apparatus (10) for moderating a skin lesion detection model (30). The apparatus (10) comprising a processor (12) and a memory (11). The processor (12) is configured to: receive user data (13) associated with a user; receive an output of the skin lesion detection model (14); modify the output of the skin lesion detection model (14) in accordance with the user data (13) to provide a modified output (15) indicative of skin lesion detection for the user; and output the modified output (15).

11 Claims, 3 Drawing Sheets

(51) Int. Cl.
 _G06T 7/00_ (2017.01)
 _G16H 50/20_ (2018.01)
(52) U.S. Cl.
 CPC .......... _A61B 5/7475_ (2013.01); _G06T 7/0014_
 (2013.01); _G16H 50/20_ (2018.01); _G06T_
 _2207/30088_ (2013.01); _G06T 2207/30096_
 (2013.01)

(56) References Cited

U.S. PATENT DOCUMENTS

| | | |
|---|---|---|
| 2011/0231205 A1 | 9/2011 | Letts |
| 2015/0178965 A1* | 6/2015 | Edwin .................... G06T 11/60 |
| | | 382/311 |
| 2015/0220504 A1 | 8/2015 | Bocanegra Alvarez |

| | | |
|---|---|---|
| 2017/0372459 A1 | 12/2017 | Tan |
| 2019/0392953 A1 | 12/2019 | Steuer |
| 2020/0170564 A1 | 6/2020 | Jiang |
| 2023/0255467 A1* | 8/2023 | Ikenoyama .......... G06T 7/0012 |
| | | 382/128 |

FOREIGN PATENT DOCUMENTS

| | | |
|---|---|---|
| WO | 2017093793 A1 | 6/2017 |
| WO | 2019191131 A1 | 10/2019 |

OTHER PUBLICATIONS

Redmon, Joseph et al "You Only Look Once: Unified, Real-Time Object Detection", 2016 IEEE Conference on Computer Vision and Pattern Recognition.

* cited by examiner

APPARATUS AND METHOD FOR MODERATING A SKIN LESION DETECTION MODEL

CROSS-REFERENCE TO PRIOR APPLICATIONS

This application is the U.S. National Phase application under 35 U.S.C. § 371 of International Application No. PCT/EP2021/084507, filed on Dec. 7, 2021, which claims the benefit of European Patent Application No. 20217603.8, filed on Dec. 29, 2020. These applications are hereby incorporated by reference herein.

FIELD OF THE INVENTION

Embodiments of the present invention relate generally to the detection of skin lesions and to the improvement of models for skin lesion detection.

BACKGROUND OF THE INVENTION

In the area of skincare, the detection of skin lesions, such as, for example, pimples, spots, rashes, macules, nodules, etc., is a desirable feature so that an individual may treat the skin lesion or apply extra care to the affected area. Early detection of a skin lesion may allow for preventative action to be taken so that the disturbance to the skin caused by the lesion may be minimized. Detection models are known and may use traditional camera technology to analyse an area of a user and detect any skin lesions. However, the accuracy of such detection models is often low, resulting in inaccurate detection results. This can diminish the user's trust in the detection model.

It is therefore desirable to improve the output of a detection model for detecting skin lesions. That is, it is desirable to improve the results of a skin lesion detection model such that the accuracy of the detection results may be improved for a user.

SUMMARY OF THE INVENTION

The invention is defined in the independent claims. Preferred embodiments are defined in the dependent claims.

According to an embodiment of a first aspect, there is provided an apparatus for moderating a skin lesion detection model, the apparatus comprising a processor and a memory, the processor configured to: receive user data associated with a user: receive an output of the skin lesion detection model: modify the output of the skin lesion detection model in accordance with the user data to provide a modified output indicative of skin lesion detection for the user; and output the modified output.

Thus, information of the user may be used to modify the output of the detection model so that the overall performance of the detection model for detecting skin lesions may be improved. The altered results of the detection model are tailored to the user and so the accuracy of the skin lesion detection provided by the apparatus may be improved. That is, the perceived accuracy of the skin lesion detection for a given user may be improved by modifying the output of the detection model using information associated with the user since the results of the detection model are altered to be more appropriate to the user. The user's trust in the detection may also be enhanced by the improved accuracy of the results with respect to the user.

The detection model may be any model for skin lesion detection such as those found in the field of skincare. The detection model may also be referred to as an automatic detection model and may be an artificial intelligence (AI) model. Such models are known in the art and analyze data to detect skin lesions. For example, the detection model may acquire image data of a user and may perform processing of the acquired image data to detect one or more skin lesions. The apparatus may acquire an image of the user (for example, via a camera associated with or included in the apparatus) and may provide the image as an input to the skin lesion detection model. The image may be referred to as assessment data. The results of the detection model may be provided as a list of detected skin lesions and associated probability scores. i.e. a confidence score of the detection. The results may be provided on an image of the user so that the user can see the locations of the detected skin lesions.

The apparatus may comprise one or more processors and processes of the apparatus may be performed by a single processor or by multiple processors in combination. A single processor may therefore perform one or more of the processes of the apparatus. The memory and the one or more processors are communicably connected, for example, via a bus. The one or more processors may store and retrieve information from the memory, such as for example, intermediate data generated when performing the processes of the apparatus.

The user may be an individual that is the subject of the skin lesion detection model. For example, the user may be an individual that uses an application for skin lesion detection on a user device, such as, for example, a smartphone. The user data may be information about the user that is relevant for assessing skin lesions detected by the detection model. The modified output may be modified detection results. That is, the modified output is the detection results of the module that have been modified in accordance with the user data such that the modified detection results are tailored to the user.

The user data may comprise one or more of: a known skin feature of the user; a known skin lesion of the user: an attention area of the user; a preference of a type of skin lesion of the user. That is, the user data may include information on a known skin feature of the user; a known skin lesion of the user; an attention area of the user: a preference of a type of skin lesion of the user, or any combination thereof. Thus, the user data may include suitable information for modifying the output of the detection model. For example, the user data may include information identifying a known skin feature of the user (such as, for example, a mole or a scar) and/or may include information identifying an attention area of the user (such as, for example, an area of the face where the user is prone to getting spots). Such information may affect the user's interpretation of the results of the detection model and is therefore relevant for moderating the results.

The user data may comprise one or more of: a location of a known skin feature of the user; a location of a known skin lesion of the user; and a location of an attention area of the user. The user data may therefore comprise an identification of a feature and/or an area and the position of said feature or area. The location may be provided as coordinates, for example, the coordinates (or range of coordinates) of an image of the user.

A known skin feature of the user may comprise one or more of: a mole, a scar, a birth mark, a freckle, and a macule. That is, a known skin feature of the user may include a mole, a scar, a birth mark, a freckle, a macule, or any combination thereof. A known skin lesion of the user may be a skin lesion, such as, for example, a pimple, which the user is aware of. For example, the user may wish to ignore a particular skin lesion and so this skin lesion should not be included in the modified output or should be provided with a low score.

The information may indicate the user's preferences with regards to the type of skin lesion that they care about and thus which skin lesion types they prefer to be notified about. Thus, the user data may include such information so that the output of the detection model may be modified to reflect this preference. The preference may be provided as a ranking list. For example, the user data may indicate that they prefer to know about pimples rather than macules, and/or prefers the detection of macules over nodules.

An attention area may be an area of interest of the user, such as an area that is prone to skin lesions, or an area considered to be important to the user, such as, for example, the face. The attention area may also be referred to as an area of importance, a priority area and/or an assessment area. An attention area may be identified by the user in the user data. Alternatively or additionally, an attention area may be automatically captured via a camera associated with the apparatus and provided to the apparatus as (part of) the user data. For example, facial recognition may be used to identify an attention area of a user.

The output of the skin lesion detection model may comprise a location of a detected skin lesion. The output of the skin lesion detection model may also comprise a probability score associated with the detected skin lesion. The output of the detection model may therefore identify the position and/or confidence score of a detected skin lesion. Multiple skin lesions may be detected and the output may comprise a location and/or probability score associated with one or more of the detected skin lesions. The probability score indicates a confidence score of the detection model in determining that the detected feature is a skin lesion. The location may be provided as coordinates, for example, the coordinates (or range of coordinates) of an image of the user at which the skin lesion is detected. The locations of the user data and/or the locations of detected skin lesions may be determined/extracted from an acquired image (or series of images) of the user.

The modified output may comprise one or more detected skin lesions. The modified output may also comprise an accompanying detection score of each of the detected skin lesions. That is, the modified output may comprise a detected skin lesion and a detection score of the skin lesion. The modified output may also comprise a location of the detected skin lesion. The detection score may reflect the modification of the probability score of the detection model with respect to the user data. The detection score may therefore provide a ranking of the detected skin lesions which reflects the user data, i.e. the user's preferences and skin features.

The detection score may, for example, be any whole or fractional number between (and including) 0 and 10. For example, a detection score of 0 may mean that the detected lesion is excluded from the modified output: a detection score of 1 may indicate a low importance level; and a detection score of 10 may indicate a high importance level. The 'importance' may relate to the importance to the user. i.e. the user's priorities.

The output of the skin lesion detection model may comprise a location of a detected skin lesion. The user data may comprise a location of a known skin feature of the user. The processor may be configured to modify the output of the skin lesion detection model by comparing the location of the detected skin lesion with the location of the known skin feature of the user. That is, the locations of the detected skin lesion and the known skin feature may be cross-referenced and the output of the skin lesion detection model modified accordingly. By comparing the locations, it may be determined that a skin feature of the user has been erroneously identified as a skin lesion by the detection model, and/or that a detected skin lesion is already known to the user. The output may therefore be modified to exclude the detected feature or to give it a low detection score. The results of the detection model may therefore be improved since erroneous detections may be identified and removed.

The processor may therefore be configured to exclude the detected skin lesion from the modified output in response to the location of the detected skin lesion corresponding to the location of the known skin feature of the user. That is, if the locations of the detected skin lesion and the known skin feature match or coincide, then the detected skin lesion may be discarded such that it is not included in the modified output. Alternatively, the detected skin lesion may be given a low detection score to reflect that the locations correspond with each other and the detected skin lesion is likely to be a known skin feature. i.e. the skin feature is erroneously identified as a skin lesion by the detection model. The locations corresponding with each other may mean that they coincide, match, overlap and/or are within a predetermined distance of each other. By discarding the detected skin lesion or giving it a low detection score when the locations correspond, the modified output may be more accurate since the erroneous detection will be filtered.

The output of the skin lesion detection model may comprise a location of a detected skin lesion. The user data may comprise a location of an attention area of the user. The processor may be configured to modify the output of the skin lesion detection model by comparing the location of the detected skin lesion with the location of the attention area of the user. That is, the locations of the detected skin lesion and the attention area may be cross-referenced and the output of the skin lesion detection model modified accordingly. By comparing the locations, it may be determined that a detected skin lesion is present in an area which has been identified as an area of importance to the user. The output may therefore be modified to reflect this and the results of the detection model may therefore be improved for the user.

The processor may be configured to provide emphasis to the detected skin lesion in the modified output in response to the location of the detected skin lesion corresponding to the location of an attention area of the user. That is, if the locations of the detected skin lesion and the attention area match or coincide, then the detected skin lesion may be emphasized so as to indicate that the lesion is positioned in an area of importance to the user. Alternatively or additionally, the detected skin lesion may be given a high detection score to reflect that the location corresponds with the attention area. The locations corresponding with each other may mean that they coincide, match, overlap and/or are within a predetermined distance of each other. By emphasizing the detected skin lesion or giving it a high detection score when the locations correspond, the modified output may be more relevant to the user. The emphasis may be provided, for example, on an image of the user, such as by highlighting the detected skin lesion. The image may be displayed for the user.

The output of the skin lesion detection model may comprise a plurality of detected skin lesions. The processor may be configured to filter the plurality of skin lesions in accordance with the user data. That is, the results of the detection model may be filtered using the user data, such that detected skin lesions that are in low importance areas (i.e. not attention areas) may be removed, known skin features may be removed, known skin lesions may be removed, and/or skin lesion types that are of low importance to the user may be removed.

The processor may be configured to store the received user data in a memory device. The user data may therefore be stored in and received from a memory device. The processor may be configured to retrieve the stored user data in a subsequent modification of an output of the skin lesion detection model. That is, the user data may be provided by the user during an initial process and stored in the memory device. In subsequent processes, the processor may retrieve the user data from the memory device such that the user does not have to provide the information again. The burden on the user may therefore be improved. The memory device may be the memory of the apparatus or may be another memory device communicably connected to the apparatus, such as, for example, a networked or cloud server.

The output of the skin lesion detection model may comprise a probability score of a detected skin lesion. The processor may be configured to modify the output of the skin lesion detection model by weighting the probability score in accordance with the user data to provide a modified probability score in the modified output. The probability score may therefore be adjusted to reflect the user data. For example, the probability of a detected skin lesion that, from the user data, is determined to likely be a known skin feature may be weighted to a low score. Conversely, a detected skin lesion located in an attention area may be weighted with a high score. The weighting may therefore reflect the user's preferences and features.

The processor may be configured to determine whether the modified probability score exceeds a predetermined threshold. The processor may be configured to generate an alert in response to the modified probability score exceeding the predetermined threshold. The processor may be configured to output the alert. Thus, if a modified probability score is greater than a predetermined threshold, an alert may be generated and output to the user. For example, the user may be alerted to a skin lesion detected in an area of importance to the user so that the user may take action, such as, by treating the detected skin lesion. The alert may be a visual notification and/or an audio notification provided to the user, for example, via a user device. For example, the alert may be provided as a visualization, such as, for example, bold and/or highlighted, on an image of the user to gain the user's attention. The user may therefore be notified of detected skin lesions that they are likely to perceive as very important.

The apparatus may also provide a recommendation to the user with respect to the detected skin lesion. For example, a treatment recommendation may be provided to the user. The user may dismiss the alert and/or recommendation, and/or request further information, e.g. from the Internet. For example, the apparatus may receive an instruction via a user interface to dismiss an alert and to search for treatment advice for the type of detected skin lesion.

The user data may be received from one or more of: a memory device: a user device associated with the user and communicably connected to the apparatus: a user interface of the apparatus; an imaging device communicably connected to the apparatus; and an audio input of the apparatus. The user data may also be received from another device comprising a camera and which captures the user's eye gaze or where the user touched on his/her face. The user data may therefore be input by the user, and/or may be retrieved from memory. The apparatus may comprise an input device configured to receive input information from the user, and may extract the user data from the input information.

The processor may be configured to acquire an image of the user. The processor may be configured to receive input information from the user. The processor may be configured to extract the user data from the image of the user in accordance with the input information received from the user. That is, an image of the user may be acquired and the user may provide input information which enables the user data to be acquired from the image. For example, the user may annotate the image through a user interface. From the annotation input by the user (such as, for example, a touch operation on a touch screen), an attention area and/or a known skin feature may be extracted from the image.

In other words, an image of the user may be acquired, and user input in which the user annotates the image may be received so as to provide the user data. The annotation may be performed on a display device or a user interface on which the image is displayed and the user provides input (such as, for example, via a touch screen and/or voice control) to identify assessment areas and/or known skin features. The user data may be acquired from the user's own annotation of a captured image, for example, annotation via a user interface (such as, a guided user interface, GUI) and display of the apparatus or another device which is communicably connected to the apparatus. The user data may therefore be provided as or extracted from image data.

The apparatus may acquire a facial image of the user and perform facial alignment of the facial image to normalize the facial image. The normalized facial image may be provided to the skin lesion detection model as an input.

The apparatus may acquire a facial image of the user and provide the facial image to the skin lesion detection model as an input. The apparatus may perform facial alignment on a facial image output from the skin lesion detection model to normalize the output facial image.

The user data may comprise a facial image of the user. The output of the skin lesion detection model may comprise an analyzed facial image of the user. The processor may align the analysed facial image of the user with the facial image of the user; and filter a detected skin lesion in the analysed facial image with an identified known feature of the user or an identified assessment area of the user in the facial image.

The modified output may be output to one or more of: a display device of the apparatus; and a transmitter of the apparatus. That is, the apparatus may comprise a display device configured to display the modified output, and/or the apparatus may comprise a transmitter configured to transmit the modified output. The transmitter may transmit the output to a user device communicably connected to the apparatus. The information may therefore be presented to the user or transmitted to another device for presentation to the user.

The processor may be configured to generate a screen of a user interface in accordance with the modified output. That is, the modified output may be provided to the user as a screen of a user interface (a GUI). Multiple screens may be generated by the processor to provide the detection results to the user. For example, a separate screen of the GUI may be generated to identify each of the detected skin lesions. If the output of the skin lesion detection model is modified in accordance with the user data (for example, to exclude known features from the detection results) then fewer GUI screens need to be generated and presented to the user. The efficiency of the apparatus may therefore be improved According to an embodiment of a second aspect, there is provided a method of moderating a skin lesion detection model, the method comprising: receiving user data associated with a user: receiving an output of the skin lesion detection model: modifying the output of the skin lesion detection model in accordance with the user data to provide a modified output indicative of skin lesion detection for the user; and outputting the modified output. The method may be computer-implemented.

According to an embodiment of a third aspect, there is provided a computer program which when executed carries out a method of moderating a skin lesion detection model, the method comprising: receiving user data associated with a user: receiving an output of the skin lesion detection model: modifying the output of the skin lesion detection model in accordance with the user data to provide a modified output indicative of skin lesion detection for the user; and outputting the modified output. The method may be computer-implemented.

Features and sub-features of the method and computer program aspects may be applied to the apparatus aspects and vice versa.

According to an embodiment of fourth aspect of the invention there is provided a non-transitory computer-readable medium storing a computer program as described above.

According to an embodiment of a fifth aspect of the invention there is provided a system comprising: a user interface for receiving user data input by a user: a skin lesion detection model for detecting skin lesions of the user: a display for displaying output information to the user and an apparatus configured to: receive the user data associated with a user: receive an output of the skin lesion detection model: modify the output of the skin lesion detection model in accordance with the user data to provide a modified output indicative of skin lesion detection for the user; and output the modified output to the display.

An apparatus or computer program according to preferred embodiments of the present invention may comprise any combination of the method aspects. Methods or computer programs according to further embodiments may be described as computer-implemented in that they require processing and memory capability.

The apparatus according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer configures the computer to become the apparatus according to any of the preceding apparatus definitions or any combination thereof.

According to a further aspect there is provided a program which when loaded onto the at least one computer configures the at least one computer to carry out the method steps according to any of the preceding method definitions or any combination thereof.

In general the computer may comprise the elements listed as being configured or arranged to provide the functions defined. For example this computer may include memory, processing, and a network interface.

The invention may be implemented in digital electronic circuitry, or in computer hardware, firmware, software, or in combinations of them. The invention may be implemented as a computer program or computer program product, i.e., a computer program tangibly embodied in a non-transitory information carrier, e.g., in a machine-readable storage device, or in a propagated signal, for execution by, or to control the operation of, one or more hardware modules.

A computer program may be in the form of a stand-alone program, a computer program portion or more than one computer program and may be written in any form of programming language, including compiled or interpreted languages, and it may be deployed in any form, including as a stand-alone program or as a module, component, subroutine, or other unit suitable for use in a data processing environment. A computer program may be deployed to be executed on one module or on multiple modules at one site or distributed across multiple sites and interconnected by a communication network.

Method steps of the invention may be performed by one or more programmable processors executing a computer program to perform functions of the invention by operating on input data and generating output. Apparatus of the invention may be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The invention is described in terms of particular embodiments. Other embodiments are within the scope of the following claims. For example, the steps of the invention may be performed in a different order and still achieve desirable results.

Elements of the invention have been described using the terms "memory", "processor", etc. The skilled person will appreciate that such terms and their equivalents may refer to parts of the system that are spatially separate but combine to serve the functions defined. Equally, the same physical parts of the system may provide two or more of the functions defined.

For example, separately defined means may be implemented using the same memory and/or processor as appropriate.

BRIEF DESCRIPTION OF THE DRAWINGS

Exemplary embodiments will now be described, by way of example only, with reference to the following drawings, in which.

DETAILED DESCRIPTION OF THE EMBODIMENTS

Figure 1:
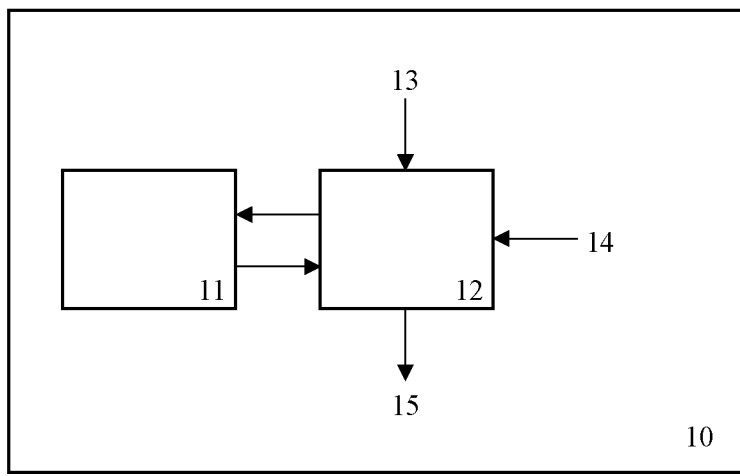
FIG. 1 is a block diagram of main apparatus components according to a general embodiment of an aspect of the invention.

Embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a." "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein may be used in the practice or testing of the embodiments.

Embodiments of aspects may provide an apparatus, method, computer program and system for moderating (the results of) a skin lesion detection model.

As discussed above, in the area of skincare, automated detection of skin lesions (such as, pimples, spots, rashes, macules, nodules etc.) using (traditional) camera technology is a desirable feature. Such skin lesions are often seen as an annoyance and (early) detection will allow the user to address/treat the lesion (for example, the pimple) and apply extra care to the affected area. However, the accuracy of detection models is often low, resulting in inaccurate detection results. In fact, reaching 100% sensitivity and specificity of pimple detection may not be possible. A recent Wizard-of-OZ user test using a trained human annotator (i.e. a skin therapist) to detect pimples has shown that even a human cannot be fully correct on detecting pimples. The accuracy of such detection models can also be greatly influenced by factors such as environment light, i.e. the lighting of an environment in which an image of a user is captured.

One particular example of a detection model is described in the paper "*You Only Look Once: Unified, Real-Time Object Detection*" by Joseph Redmon, Santosh Kumar Divvala, Ross B. Girshick and Ali Farhadi, ArXiv 1506.02640, 2015. This paper describes a technique to efficiently estimate object bounding boxes from an image using a neural network. If this neural network architecture is trained on different types of skin lesions, it would depict the locations (by means of bounding boxes) and associated probability of the skin lesions, for all detected skin lesions.

In a detection model, the detection accuracy may be affected by a number of factors, including poor camera quality, capturing settings, environment lighting and/or non-differentiating skin features. It is very difficult to account for these factors in the model training phase. On the other hand, users have knowledge of areas in which they often have skin lesions. Furthermore, users may likely have their own focused areas which are important and in which the presence of pimples/lesions are particularly undesirable. For example, a user may consider lesions/pimples on the face to be more annoying than lesions/pimples in other areas of the body.

It is, however, difficult to build user's own knowledge and focused areas into models for skin lesion detecting. In the same user test mentioned above, about 10 out of 15 users indicated that they have focused areas to check pimples. They tend to check the focused areas first and act on (such as, for example, by pushing out or cleaning) the lesions/pimples in these areas.

Detection models may also erroneously detect skin features (such as, for example, moles, birthmarks, scars, etc.) as lesions/pimples. Such erroneous detection reduces the accuracy of the model and may diminish the user's trust in the detection model. That is, if a detection system keeps on detecting these (permanent) skin features as skin lesions, the user may not trust the system and may stop using the detection application.

It is therefore desirable to improve the results of a skin lesion detection model such that the accuracy of the detection results may be improved for a user. According to embodiments of aspects, this may be achieved by moderating a skin lesion detection model using data associated with the user. The user's knowledge may therefore be combined with detection algorithms to improve the perceived performance of the detection system and to generate targeted recommendations in the future. Improvement of the actual detection model is beyond the scope out of this disclosure and embodiments of aspects provide means for moderating the results of detection models to provide detection results that are specific to the user. Moderating of the results may also be considered as regulating, refining, adjusting and/or calibrating the results of the detection model.

Embodiments of aspects may provide a method to generate a score for detected skin lesions by combining a user's knowledge and skin lesion detection algorithms. As stated above, for home-use skin lesion detection applications, even a human annotator cannot be 100% accurate in skin lesion detection. On the other hand, a user has good knowledge of their own skin features (for example, moles) and areas which are prone to skin lesions and often have pimples appearing. The perceived performance of the detection model may therefore be optimized by combining user knowledge with the output of a skin lesion detection algorithm.

FIG. 1 shows a block diagram of information flow into main apparatus components in apparatus 10. The apparatus 10 comprises a memory 11 and a processor 12. The processor 12 receives user data 13 associated with a user and also receives an output of the skin lesion detection model 14. The processor 12 modifies the output of the skin lesion detection model 14 in accordance with the user data 13 to provide a modified output 15 indicative of skin lesion detection for the user and the processor 12 outputs the modified output 15.

The apparatus may be a suitable processing device that is capable of being communicably connected to other devices. The device may, for example, be a smartphone associated with the user. Additionally, the apparatus may be provided as part of a cloud computing network such that some of the processing is performed in the cloud.

Figure 2:
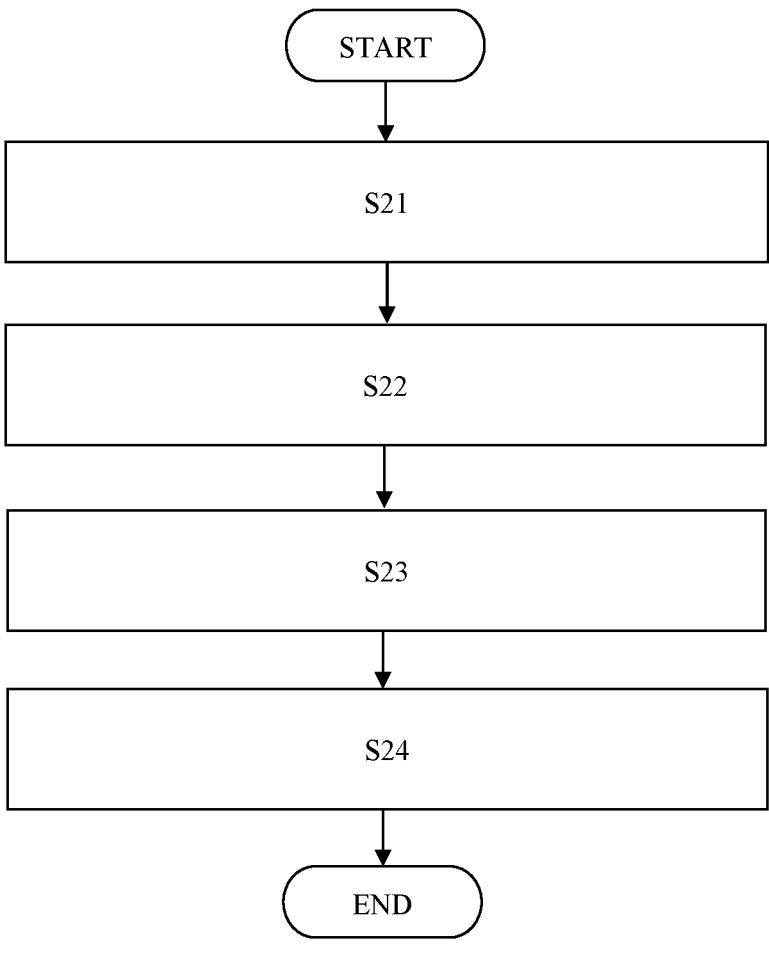
FIG. 2 is a flowchart of a method according to a general embodiment of an aspect of the invention.

FIG. 2 shows a flow chart representing the method according to a general embodiment of an aspect of the invention. Firstly, in step S21, user data associated with a user is received and an output of the skin lesion detection model is received at step S22. At step S23 the output of the skin lesion detection model is modified in accordance with the user data to provide a modified output indicative of skin lesion detection for the user. Finally, the modified output is output at step S24.

Figure 3:
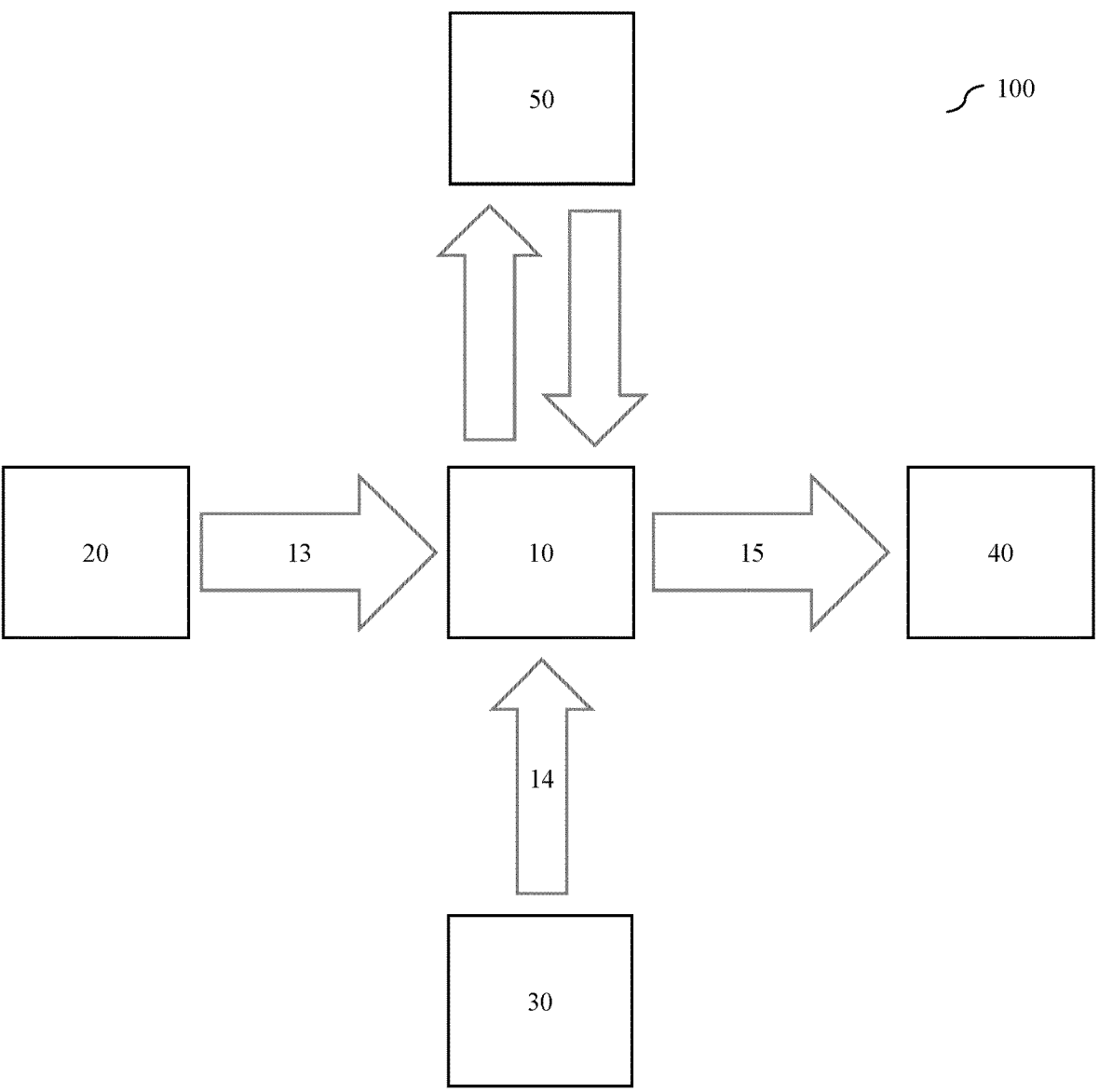
FIG. 3 is a block diagram of a system according to an embodiment of an aspect of the invention.

FIG. 3 shows a block diagram of a system according to an embodiment of an aspect of the invention. The system 100 comprises an apparatus 10, a user interface 20, a detection model 30, a display 40 and a memory 50. The user interface 20 receives user data 13 input by the user. The user interface 20 may, for example, be a touch screen (of a device such as a smartphone) that displays an image of the user and receives input from the user so that the image is annotated. The user data 13 may be information identifying known skin features and/or particular areas of interest of the user. Additionally or alternatively, the user data 13 may be information identifying a known skin lesion of the user and/or a user preference of a type of skin lesion. The apparatus 10 receives the user data 13 from the user interface 20 and an output 14 of the detection model 30. The apparatus 10 modifies the output 14 of the detection model 30 in accordance with the user data 13 to provide a modified output 15. For example, a known skin feature identified in the user data 13 may be erroneously detected as a skin lesion by the detection model 30. The apparatus 10 may therefore modify the detection results 14 of the model 30 to reflect that the identified skin lesion is actually a known skin feature, such as, for example, a mole, identified in the user data 13. The known skin feature may therefore be removed from the modified output 15. The modified output 15 is then provided to the display 40, such that the detection results modified according to the user data 13 are provided to the user.

The user data 13 may be stored in the memory 50 and retrieved from the memory 50 by the apparatus 10. Thus, the user data 13 may be received from the memory 50 additionally or alternatively to the user interface 20. The user data 13 may therefore be input by the user via the user interface 20 at an initial/calibration operation and then stored in the memory 50. In a subsequent operation, the user data 13 may be retrieved from the memory 50 by the apparatus 10 such that the user does not have to input the user data 13 each time the detection model 30 is run. The determinations may therefore be performed more quickly and the burden on the user may be reduced. The memory 50 may be a memory of the apparatus 10 or may be another memory device, for example, associated with the apparatus 10 and/or may be received from another device, such as, for example, a network or cloud server.

The arrangement of the elements in FIG. 3 are provided for demonstration purposes only. That is, although the elements in FIG. 3 are shown as separate entities, the elements may be provided as one or more single devices that each provide one or more of the listed elements. The system elements may be provided as a user device, such as, for example, a smartphone. That is, the user may use a smartphone to acquire an image of themselves, they may then annotate the image using the touchscreen or microphone (voice input) of the smartphone to provide the user data. The acquired image may be used by a detection model installed on the device to detect skin lesions and the device may modify the detection results in accordance with the user data to provide the modified output. The modified output may then be output to the display of the smartphone. The modified output may be displayed as an image of the user in which the modified results are marked on the image. Alternatively or additionally to the visual output, the output may be provided as an audio output or may trigger further processing of the smartphone. For example, the modified output may trigger an internet search for appropriate skin lesion treatments and/or may trigger a process for the user to order products for treatment of the detected skin lesions.

Embodiments of the present invention may therefore improve the results of the detection model for detecting skin lesions, such that the accuracy of the detection results may be improved for a user.

According to an embodiment of an aspect, a method that provides a scoring mechanism on the detected pimples or lesions may be provided. Such a scoring mechanism combines output from an automatic detection model with user input. The output of the described model provides a score that incorporates the probability of skin lesion detection and is also directed to considerations of the user, such as areas that the user cares about.

For example, by modifying the output of the detection model using the user data, a detected skin lesion that was assigned a low probability by the detection model (i.e. a low chance of being a pimple/a low confidence score) may be given a high score if it is located in a particular area of interest identified by the user data. Conversely, a detected lesion that was assigned a high probability by the detection model may be given a low score in the modified output if the location coincides with the location of a known skin feature since it is very likely that the detection model has falsely identified the known skin feature as a sin lesion. Thus, emphasis may be provided to detected lesions in an area of interest of the user and/or the detected skin features that are erroneously detected as lesions by the model may be discarded. Similarly, a skin lesion that is known to the user may also be given a low score in the modified output. The user may also set preferences of types of skin lesion such that certain types of detected skin lesion that the user cares more about are given a higher score than other types of detected skin lesions that the user is less interested in. The perceived performance of the detection model to the user may therefore be improved.

Figure 4:
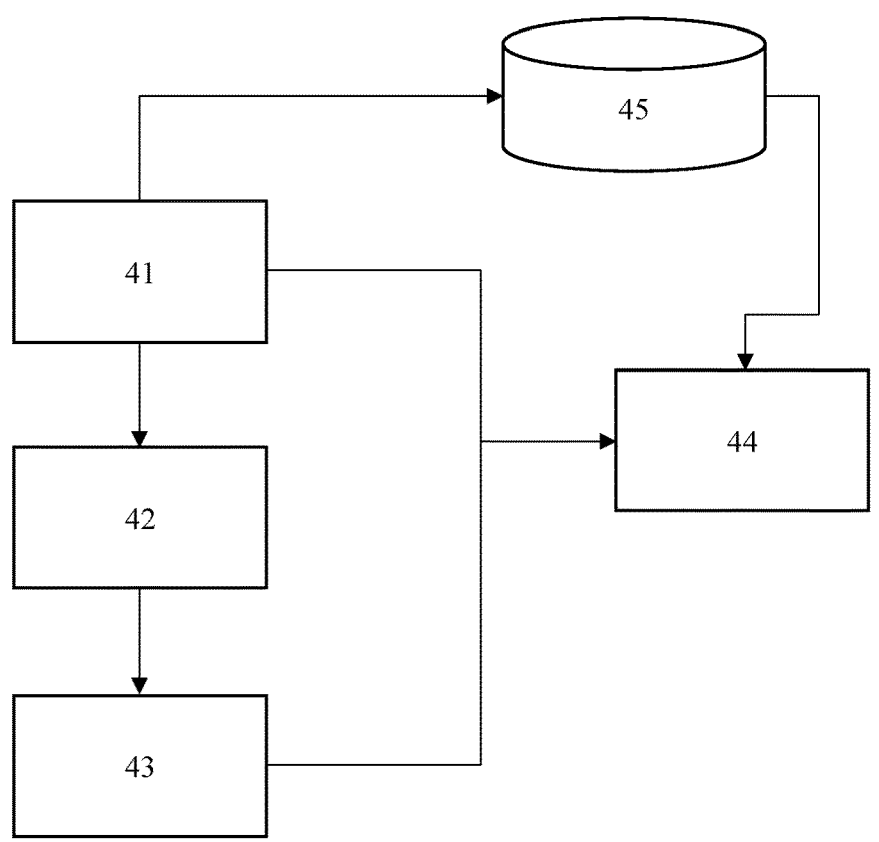
FIG. 4 is a flow diagram of a process flow according to an embodiment of an aspect of the invention.

FIG. 4 shows a flow diagram of a process flow according to an embodiment of an aspect of the invention. The process comprises the following modules:

Collecting user input 41, for example, frequent or attention areas, moles, birth marks, etc.;

Facial alignment and pimple/lesion localization 42

Skin lesion detection 43

Generating detection score 44

Knowledge base 45

Collecting User Input (User Data)

The user input may be collected from a skin detection application (for example, provided on a user device such as a smartphone) using images and videos (i.e. a sequence of images). The input may include any of the following, or any combination thereof:

Specific areas on the face or body, where the user often has pimples or lesions and/or where the user cares about.

Permanent skin features that are known to the user, such as, for example, birth marks, moles, etc.

Newly appearing permanent (or semi-permanent) skin features, such as, for example, scars which may result from pushing out pimples.

A user may click on a measurement image and annotate it to identify an attention area or a skin feature (for example, a mole). Alternatively or additionally, the user data may be provided using voice controlled input.

Facial Alignment and Pimple/Lesion Localization

This module is employed to match the location of detected pimples or lesions over various measurements. When combined with the user input, it can know whether the detected pimples or lesions are inside the indicated area (attention area) or are permanent skin features (for example, birthmarks or scars). Facial alignment may be applied as a pre-processing or as a post-processing step. In the first case, an acquired image of the face of the user is first normalized is modified to reflect the importance of the area to the user. The detection score is therefore a high score '9' in accordance with the user's focus or subjective interest. The location of pimple 2 is similar to that of pimple 3. However, the probability from the detection model is very low and so the detection score is increased to reflect the location in relation to the user attention area but is limited to a medium level due to the low probability. The method may therefore provide a balance between the objective measurement and the subjectivity characterized by the user data.

TABLE 1

| | | | An example of output data of system modules | | |
|---|---|---|---|---|---|
| Pimple Sequence | Coordinates on the Aligned Image | User Input: Attention Area (Yes/No) | Pimple Probability (from the Detection Model) | User Input: Other Features | Detection Score (e.g. 0 to 10) |
| 1 | 654,1023 | No | 87% | Mole | 0 |
| 2 | 20,676 | Yes | 12% | | 4 |
| 3 | 30,655 | Yes | 43% | | 9 |
| 4 | 672,892 | No | 90% | | 9 | to a standard view. For example, if the image was taken under a small angle, it is first corrected (to the extent possible) such that it results in a frontal view image. Then, on this normalized image, detection is applied. In the second case, detection is applied on the original image (for example, the image under a small angle), then the locations of detections (for example, pimples) are transformed to a normalized location in the alignment phase.

Skin Lesion Detection

It is a single or combination of image-based algorithms that detect specific types of skin lesions. Examples include pimple detection, skin inflammation detection and blackhead detection algorithms. The algorithms process the aligned images from the facial alignment module (or, alternatively, the acquired images that have not been aligned in the case that the normalization is performed after the detection) and output a list of detected skin lesions with their locations and probabilities.

Creating Detection Score

It is assumed that the pimple or lesion detection model outputs an unfiltered list of detected pimples (or lesions) with a probability score, along with their (normalized) locations on the face or body of the user. The output list is then modified in accordance with the user data so as to provide a modified output in which a new score is given to each of the detected pimples/lesions.

An example of pimple detection and modified scores is shown in Table 1. As can be seen from Table 1, pimple 1 was detected as 'likely a pimple' from the pimple detection model since the probability score is high. However, the location of pimple 1 corresponds to the location of a mole (a known skin feature) indicated by the user in the user data. According to the knowledgebase, 'mole is not a pimple', and so the result is modified to provide a score of 0. Pimple 4 is 'likely a pimple' and no other indication from the user was provided, and so the score of pimple 4 reflects the probability score provided by the detection model. That is, the output is not modified.

Pimple 3 is not determined to be highly probable by the detection model. However, it is located inside an attention area identified by the user in the user data and so the output A simple exemplary metric for calculating the detection score (i.e. modifying the output) is shown below, with explanations indicated by '//'.

```
if attention_area == False: //if it is not in the attention area
    if other_feature != "": //and if it is a permanent skin feature
        detection_score = 0 //it is not a pimple, therefore 0
    else: //if it is not in the attention area and not a permanent skin feature
    // then down-scale the score and still maintain it between 0 and 10
        detection_score = clip(round(0.15 * probablity_percentage + 2.5), 0,
10)
else: //if it is in the attention area
    // then up-scale the score and still maintain it between 0 and 10
    detection_score = clip(round(0.25 * probability_percentage - 13.0), 0,
10)
```

The above metric is provided as an example only and many alternative metrics may be devised. For example, in another embodiment of an aspect, the user may indicate attention areas. Then, depending on whether a detected pimple is in an attention area, the probability may be scaled (as detection score). If the detected pimple is in an attention area, the probability remains unchanged (for example, detection score=probability). On the other hand, if the detected pimple is outside of an attention area, the probability is scaled down (for example, detection_score=gain*probability: where gain <1.0). Detected lesions/pimples that are not located in attention areas may therefore be given a low score rating that is in line with the probability of the detection model.

Thus, the output from a skin detection algorithm may be combined with user input and a quantification that determines selection of skin lesion detection may be generated. Embodiments of aspects may be provided as a module in a skin measurement application and/or with a skin measurement device. It may be used to control the amount of pimple/lesion detection provided to the user, thereby enabling the user to focus on monitoring or treatment areas.

Embodiments of aspects may therefore provide an apparatus and method for moderating (an output of) a detection model for detecting skin lesions. Information of the user may be used to modify the output of the detection model so that the overall performance of the detection model for detecting skin lesions may be improved. The altered results of the detection model are tailored to the user and so the accuracy of the skin lesion detection provided by the apparatus may be improved. The user's trust in the detection may also be enhanced by the improved accuracy of the results with respect to the user.

Figure 5:
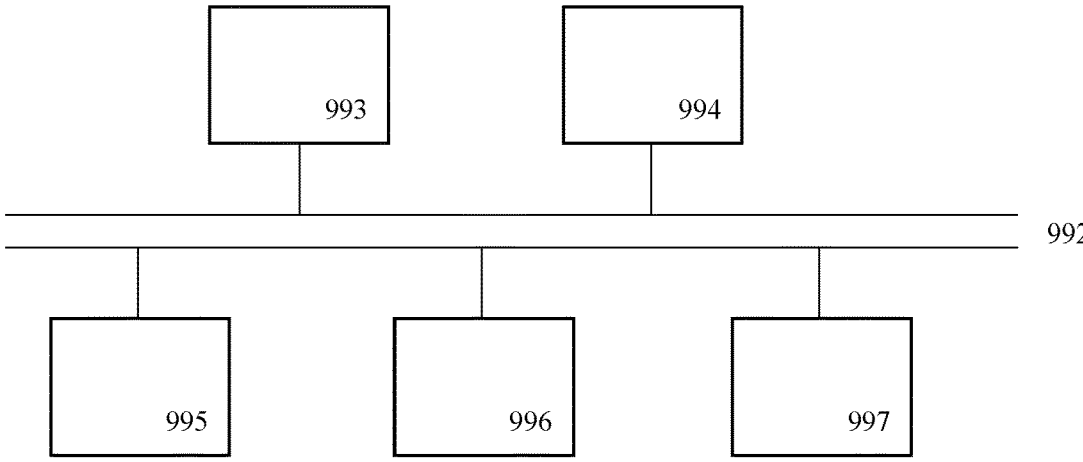
FIG. 5 is a hardware diagram illustrating hardware that may be used to implement invention embodiments.

FIG. 5 is a block diagram of a computing device, such as a server incorporating resources suitable for skin lesion detection processing, which may embody the present invention, and which may be used to implement some or all of the steps of a method embodying the present invention, and perform some or all of the tasks of an apparatus of an embodiment. For example, the computing device of FIG. 5 may be used to implement all, or only some, of steps S21 to S24 of the method illustrated in FIG. 2, to perform all, or only some, of the tasks of the apparatus shown in FIG. 1 to perform all, or only some, of the tasks of memory 11 and/or processor 12, and to perform all, or only some, of the tasks of the system shown in FIG. 3. The computing device comprises a processor 993, and memory 994, and to implement all, or only some, of steps of the process illustrated in FIG. 4. Optionally, the computing device also includes a network interface 997 for communication with other computing devices, for example with other computing devices of invention embodiments.

For example, an embodiment may be composed of a network of such computing devices. Optionally, the computing device may also include one or more input mechanisms 996 such as a keyboard and mouse for the user to input any of, for example, user data or an image for analysis, and a display unit 995 such as one or more monitors. The display unit may show a representation of data stored by the computing device for instance, representations of the received user data and/or the modified output of the detection. The display unit 995 may also display a cursor and dialogue boxes and screens enabling interaction between a user and the programs and data stored on the computing device. The input mechanisms 996 may enable a user to input data and instructions to the computing device. The components are connectable to one another via a bus 992.

The memory 994 may include a computer readable medium, which term may refer to a single medium or multiple media (e.g., a centralized or distributed database and/or associated caches and servers) configured to carry computer-executable instructions or have data structures stored thereon. Computer-executable instructions may include, for example, instructions and data accessible by and causing a general purpose computer, special purpose computer, or special purpose processing device (e.g., one or more processors) to perform one or more functions or operations. Thus, the term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media. By way of example, and not limitation, such computer-readable media may include non-transitory computer-readable storage media, including Random Access Memory (RAM). Read-Only Memory (ROM). Electrically Erasable Programmable Read-Only Memory (EEPROM). Compact Disc Read-Only Memory (CD-ROM) or other optical disk storage, magnetic disk storage or other magnetic storage devices, flash memory devices (e.g., solid state memory devices).

The processor 993 is configured to control the computing device and execute processing operations, for example executing code stored in the memory to implement the various different functions described here and in the claims. The memory 994 stores data being read and written by the processor 993, such as the inputs (such as, for example, the user data), interim results (such as, for example, the output of the detection model) and results of the processes referred to above (such as, for example, the modified output). As referred to herein, a processor may include one or more general-purpose processing devices such as a microprocessor, central processing unit, or the like. The processor may include a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor may also include one or more special-purpose processing devices such as an application specific integrated circuit (ASIC), a field programmable gate array (FPGA), a digital signal processor (DSP), network processor, or the like. In one or more embodiments, a processor is configured to execute instructions for performing the operations and steps discussed herein.

The display unit 995 may display a representation of data stored by the computing device and may also display a cursor and dialog boxes and screens enabling interaction between a user and the programs and data stored on the computing device. The input mechanisms 996 may enable a user to input data and instructions to the computing device. The display unit 995 and input mechanisms 996 may form the output 26.

The network interface (network I/F) 997 may be connected to a network, such as the Internet, and may be connectable to other such computing devices via the network. The network I/F 997 may control data input/output from/to other apparatus via the network. Other peripheral devices such as microphone, speakers, printer, power supply unit, fan, case, scanner, trackerball etc. may be included in the computing device.

Methods embodying the present invention may be carried out on a computing device such as that illustrated in FIG. 5. Such a computing device need not have every component illustrated in FIG. 5 and may be composed of a subset of those components. A method embodying the present invention may be carried out by a single computing device in communication with one or more data storage servers via a network. The computing device may be a data storage itself storing the input content before and after processing and thus for example, the dialogue and/or trained model.

A method embodying the present invention may be carried out by a plurality of computing devices operating in cooperation with one another. One or more of the plurality of computing devices may be a data storage server storing at least a portion of the data.

Other hardware arrangements, such as laptops, iPads and tablet PCs in general could alternatively be provided. The software for carrying out the method of invention embodiments as well as input content, and any other file required may be downloaded, for example over a network such as the internet, or using removable media. Any dialogue or trained model may be stored, written onto removable media or downloaded over a network.

The invention embodiments may be applied to any field in which detection of skin lesions is desired. The invention embodiments may preferably applied to the skincare and cosmetic fields, and particularly to the field of home use skin lesion detection systems.

Variations to the disclosed embodiments may be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The above-described embodiments of the present invention may advantageously be used independently of any other of the embodiments or in any feasible combination with one or more others of the embodiments.

The invention claimed is:

1. An apparatus for moderating detection results output by a skin lesion detection model, configured to detect one or more skin lesions in image data of the user, the apparatus comprising a processor and a memory, the processor configured to:

receive user data associated with a user, wherein the user data comprises a location of a known skin feature or attention area of the user prone to said one or more skin lesions, and wherein said known skin feature is of a type different from said one or more skin lesions;

receive detection results output by the skin lesion detection model, wherein the detection results output by the skin lesion detection model comprises a location of a detected skin lesion;

modify the detection results output by the skin lesion detection model in accordance with the user data to provide a modified output indicative of skin lesion detection for the user by:

comparing the location of the detected skin lesion with the location of the known skin feature or attention area of the user to determine whether the location of the detected skin lesion corresponds to the location of the known skin feature or attention area of the user; and excluding the detected skin lesion from the modified output in response to the location of the detected skin lesion corresponding to the location of the known skin feature of the user; or reflecting that the detected skin lesion is within the location of the attention area of the user in response to the location of the detected skin lesion corresponding to the location of the attention area of the user; and output the modified output for a display, such that the modified detection results are provided to the user in an image of the user so that the user can see the location(s) of the detected one or more skin lesions of the modified detection results.

2. The apparatus of claim 1, wherein the user data further comprises one or more of:

a known skin feature of the user
a known skin lesion of the user;

an attention area of the user; and
a preference of a type of skin lesion of the user.

3. The apparatus of claim 1, wherein the output of the skin lesion detection model comprises a location of a detected skin lesion and a probability score associated with the detected skin lesion.

4. The apparatus of claim 3, wherein the modified output comprises one or more detected skin lesions and an accompanying detection score of each of the detected skin lesions.

5. The apparatus of claim 1, wherein the processor is configured to store the received user data in a memory device.

6. The apparatus of claim 1, wherein
the output of the skin lesion detection model comprises a probability score of a detected skin lesion; and
the processor is configured to modify the output of the skin lesion detection model by weighting the probability score in accordance with the user data to provide a modified probability score in the modified output.

7. The apparatus of claim 6, wherein the processor is configured to:

determine whether the modified probability score exceeds a predetermined threshold;

generate an alert in response to the modified probability score exceeding the predetermined threshold; and output the alert.

8. The apparatus of claim 1, wherein the user data is received from one or more of:

a memory device;
a user device associated with the user and communicably connected to the apparatus;
a user interface of the apparatus;
an imaging device communicably connected to the apparatus; and
an audio input of the apparatus.

9. The apparatus of claim 1, wherein the processor) is configured to:

acquire an image of the user;
receive input information from the user; and
extract the user data from the image of the user in accordance with the input information received from the user.

10. A method of moderating detection results output by a skin lesion detection model configured to detect one or more skin lesions in image data of the user, the method comprising:

receiving user data associated with a user, wherein the user data comprises a location of a known skin feature or attention area of the user prone to said one or more skin lesions, and wherein said known skin feature is of a type different from said one or more skin lesions;

receiving detection results output by the skin lesion detection model, wherein the detection results output by the skin lesion detection model comprises a location of a detected skin lesion;

modifying the detection results output by the skin lesion detection model in accordance with the user data to provide a modified output indicative of skin lesion detection for the user by;

comparing the location of the detected skin lesion with the location of the known skin feature or attention area of the user to determine whether the location of the detected skin lesion corresponds to the location of the known skin feature or attention area of the user; and excluding the detected skin lesion from the modified output in response to the location of the detected skin lesion corresponding to the location of the known skin feature of the user; or reflecting that the detected skin lesion is within the location of the attention area of the user in response to the location of the detected skin lesion corresponding to the location of the attention area of the user; and outputting the modified output for a display, such that the modified detection results are provided to the user in an image of the user so that the user can see the location(s) of the detected one or more skin lesions of the modified detection results.

11. A non-transitory computer-readable storage medium storing instructions that, when executed by one or more processors, cause the processors to perform a method of moderating detection results output by a skin lesion detection model configured to detect one or more skin lesions in image data of a user, the method comprising:

receiving user data associated with the user, wherein the user data comprises a location of a known skin feature or attention area of the user prone to said one or more skin lesions, and wherein said known skin feature is of a type different from said one or more skin lesions;

receiving detection results output by the skin lesion detection model, wherein the detection results output by the skin lesion detection model comprises a location of a detected skin lesion;

modifying the detection results output by the skin lesion detection model in accordance with the user data to provide a modified output indicative of skin lesion detection for the user by;

comparing the location of the detected skin lesion with the location of the known skin feature or attention area of the user to determine whether the location of the detected skin lesion corresponds to the location of the known skin feature or attention area of the user; and excluding the detailed skin lesion from the modified output in response to the location of the detected skin lesion corresponding to the location of the known skin feature of the user; or reflecting that the detected skin lesion is within the location of the attention area of the user in response to the location of the detected skin lesion corresponding to the location of the attention area of the user; and outputting the modified output for a display, such that the modified detection results are provided to the user in an image of the user so that the user can see the location(s) of the detected one or more skin lesions of the modified detection results.

\* \* \* \* \*